United States Patent [19]

Hixon, Jr. et al.

[11] Patent Number: 5,685,987
[45] Date of Patent: Nov. 11, 1997

[54] METHOD FOR RECYCLING FORMALIN

[75] Inventors: Leonard Lee Hixon, Jr., Dalton; Joe Edward Taylor, Lookout Mtn., both of Ga.; John Joseph Matthews Rees, Signal Mnt.; Michael Robert Lafriniere, Hixon, both of Tenn.

[73] Assignees: Tresco, LLC, Chattanooga; Vision Medical, Inc., Hixson, both of Tenn.

[21] Appl. No.: 718,866

[22] Filed: Sep. 24, 1996

[51] Int. Cl.$^6$ .................. B01D 65/02; B01D 65/00; A01N 1/00

[52] U.S. Cl. .................. 210/636; 27/11; 95/273; 210/651; 210/739; 210/806; 422/36

[58] Field of Search .................. 134/10, 13, 111; 210/87, 90, 93, 137, 143, 167, 192, 195.2, 198.1, 257.2, 258, 259, 321.69, 424, 434, 636, 637, 651, 652, 663, 669, 739, 743, 748, 760, 805, 806; 422/28, 36, 306, 1; 239/416.5, 417.3; 27/11

[56] References Cited

U.S. PATENT DOCUMENTS

| | | | |
|---|---|---|---|
| 3,938,287 | 2/1976 | Gauchard | 27/11 |
| 4,072,610 | 2/1978 | Gow et al. | 210/259 |
| 4,342,651 | 8/1982 | Ahrens | 422/36 |
| 4,610,790 | 9/1986 | Reti et al. | 210/636 |
| 4,787,980 | 11/1988 | Ackermann et al. | 210/195.2 |
| 5,078,864 | 1/1992 | Whittier | 210/259 |
| 5,217,622 | 6/1993 | Flores | 210/188 |
| 5,252,304 | 10/1993 | Miyoshi | 422/36 |
| 5,512,178 | 4/1996 | Dempo | 210/195.2 |

FOREIGN PATENT DOCUMENTS 7303928  9/1974  Netherlands .................. 27/11

Primary Examiner—Joseph W. Drodge
Attorney, Agent, or Firm—Parkhurst, Wendel & Burr, LLP

[57] ABSTRACT

A formalin fluid recycler has a combination triple pipe nozzle for introducing dirty fluid into the recycler and for expelling concentrate and permeate fluid therefrom. Dirty fluid is pumped through a strainer, filtration module and charcoal filter to purify and clarify the dirty fluid. The formalin fluid can be recirculated in the system via the nozzle or be directed to a clean receptacle. Dirty formalin fluid is further cleansed by Ozone and ultraviolet light. Percent concentration and pH level of clean recycled formalin fluid is adjusted outside of the main recycling loop. Cleaning and preservative solutions are circulated through the recycler when necessary.

11 Claims, 4 Drawing Sheets

FIG. 2a
FIG. 2b
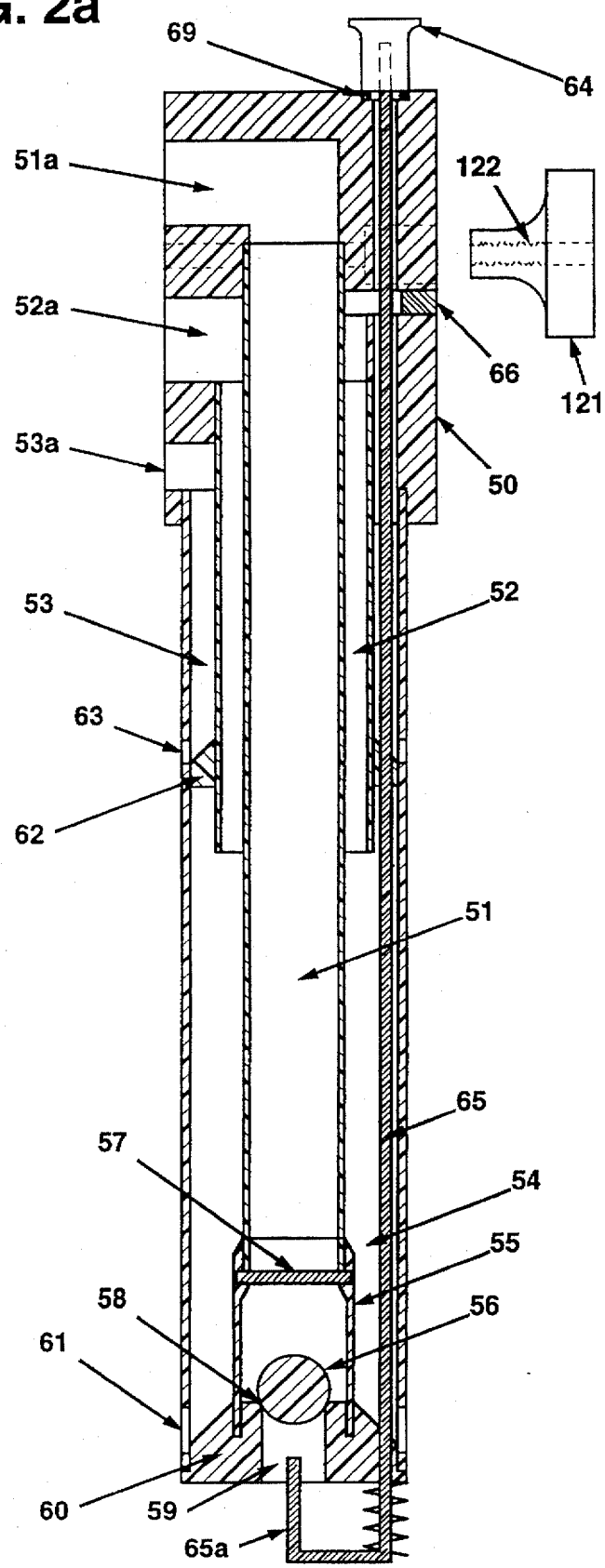
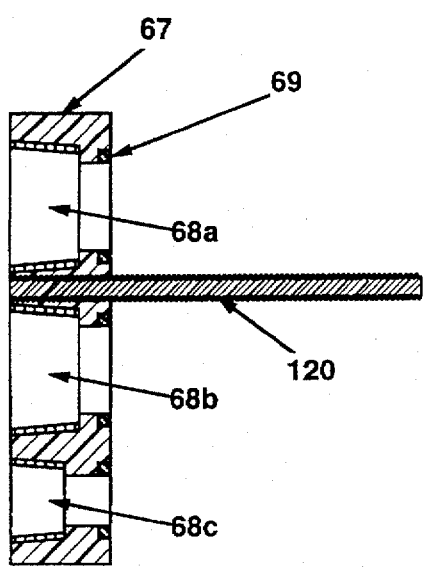

METHOD FOR RECYCLING FORMALIN

BACKGROUND OF THE INVENTION

The present invention relates to hazardous chemical solution recycling. Generally, recycling comprises taking a particle-containing fluid and processing it to remove the particles suspended therein such that the remaining fluid can be reused. Chemical solution recycling is necessary to, for example, comply with environmental regulations and reduce costs of obtaining virgin chemical solutions from producers. The present invention is directed to an apparatus and method for recycling particle-containing fluid, in particular formalin.

Formalin is comprised of 37 percent, by weight, aqueous solution of formaldehyde with a small amount of methanol. Formaldehyde is actually a colorless gaseous compound, the simplest aldehyde, suspended in an aqueous mixture. This gas (HCHO) is used to manufacture melamine and phenolic resins, polyurethane foams, fertilizers, dyes and embalming fluids. The liquid is also used as a preservative and disinfectant.

One liquid often requiring recycling at hospitals is formalin further diluted with water to a level from 37% to approximately 3.7% formaldehyde. This solution is used in the pathology departments of hospitals and morgues as a preservative type liquid for tissue and organ samples. Samples suspended in this solution can therefore be dissected and inspected well after being removed from the host. Samples stored in this solution can also be saved for future reference.

Contaminated formalin, however, is designated as a hazardous waste in some states and is prohibited from being disposed of into the city sewer system and, thus, requires expensive waste disposal techniques.

Also, contaminated formalin is considered a biohazard by the Environmental Protection Agency. Moreover, formaldehyde is considered a carcinogen by the Food and Drug Administration. That is, any ingestion, physical skin contact and inhalation thereof can cause cancer.

Formalin can be recycled by distilling. However, this method has the drawbacks of requiring heat and of producing dangerous fumes. The boiled formalin solution tends to drive the formaldehyde gas out of the Formalin solution and amplify the possibility of inhalation exposure.

SUMMARY OF THE INVENTION

The present invention provides a recycling system and method that purifies particle-containing solution to a degree sufficient that the cleansed solution can be reused as though it was virgin solution.

An object of the present invention is to provide a recycling system and method designed to recover spent and dirty formalin after use in specimen jars and laboratory equipment.

Another object of the present invention is to provide a recycling system and method that does not rely on heat and thereby reduces the hazards of fumes.

The formalin recovery system and process of the present invention reduces hazardous waste disposal costs, reduces the expense of purchasing virgin formalin and helps the environment by reusing existing formalin.

Moreover, the present invention reduces off-gassing of the formalin solution by avoiding the use of heat to distill the liquid into a pure state.

A series of high technology filtration, clarification and purification techniques are used to cleanse the contaminated solution and return the fluid back to its original color. This low energy consumption method utilizes a fully closed piping system in order to minimize the operator's exposure to both liquid and vapor during processing.

In particular the invention provides inlet means for introducing particle-containing fluid, first outlet means for discharging at least concentrate or permeate, second outlet means for discharging permeate, and a pump having an input and an output, the output being connected to the inlet means. Additionally, filtration means is provided for filtering the particle-containing fluid. The filtration means comprises an input connected to the output of the pump, a concentrate output and a permeate output, the concentrate output being connected to the first outlet means. Finally, a charcoal filter having an input connected to the permeate output, and an output, and routing means, connected to the charcoal filter output, for routing the permeate to either the first outlet means or second outlet means are provided.

The invention further provides a unique nozzle for drawing fluid from and introducing fluid into a receptacle having a first tube having a first open end and an opposed second end having a valve disposed therein, wherein fluid is drawn from the receptacle through the valve, a second tube disposed substantially coaxially with and radially outwardly of the first tube, the second tube having a first open end and an opposed second open end, wherein a first fluid is introduced into the receptacle through the second open end of the second tube, and a third tube disposed substantially coaxially with and radially outwardly of the second tube, the third tube having a first open end and an opposed second open end, wherein a second fluid is introduced into the receptacle through the second end of the third tube.

The present invention also provides a method of recycling formalin, comprising the steps of (1) pumping a particle-containing fluid from a dirty tank through a first strainer thereby removing large particles, (2) filtering the fluid through a filtration module to remove finer particles not strained by the strainer, (3) directing concentrate passed by the filtration module back to the dirty tank, and (4) routing permeate resulting from the filtering step (2) to one of the dirty tank, a clean tank and a charcoal filter.

BRIEF DESCRIPTION OF THE DRAWINGS

FIGS. 2a–b show the triple pipe nozzle of the present invention.

DETAILED DESCRIPTION OF THE INVENTION

Figure 1:
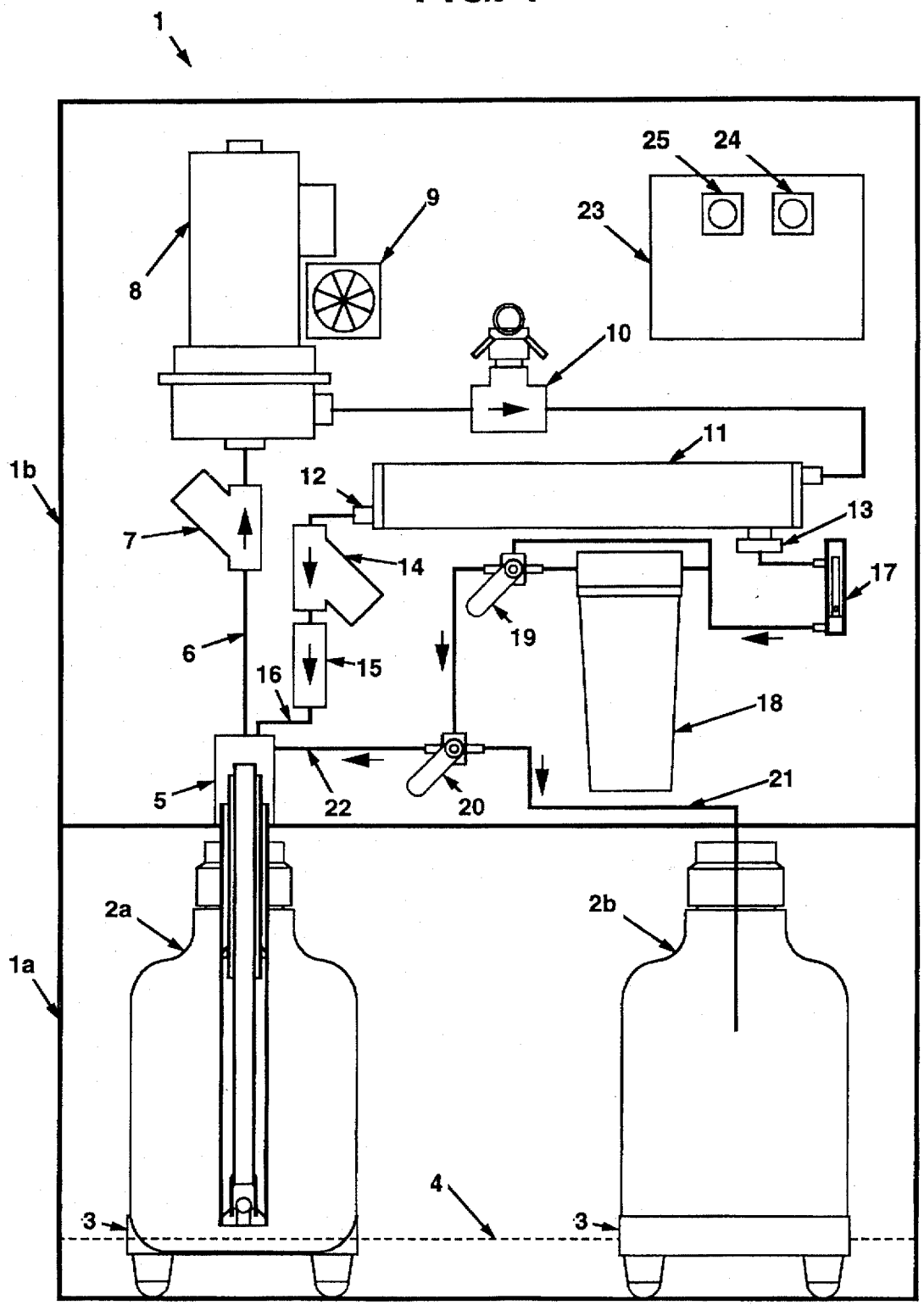
FIG. 1 shows an arrangement of the recycler according to a first embodiment of the invention.

FIG. 1 shows one embodiment of the recycler of the present invention. The recycler is accommodated in a housing 1 having upper 1a and lower 1b compartments. The lower compartment houses a dirty liquid receptacle 2a and a clean liquid receptacle 2b. Each of the receptacles is positioned on carts 3 to allow the receptacles to be moved into and out of lower housing 1a. A drip pan 4 is positioned in the base of housing 1a to retain any material that might spill or leak from the recycler or receptacles.

A triple pipe nozzle 5 is secured to the opening of receptacle 2a to draw contaminated liquid from the receptacle, return filtered concentrate back to the receptacle, and return filtered permeate back to the receptacle during multiple stage filtering and cleaning. Nozzle 5 will be explained in more detail later herein with reference to FIGS. 2a and 2b.

The main portion of the recycler is positioned in upper housing 1b. Contaminated fluid to be treated is drawn from receptacle 2a through nozzle 5, conduit 6 and Y-strainer 7 via suction action of a circulation pump 8. Y-strainer 7 removes any large particles of material. Preferably, strainer 7 is a 20 mesh (1/32" holes) filter. Further protection can be obtained by using an additional filter vessel (not shown) for trapping particles down to 5 microns using, for example, a polypropylene yarn-wound filter cartridge. The primary purpose of strainer 7 is to prevent damage to and increase the life of downstream filtration module (explained later herein).

The contaminated fluid now passes through circulation pump 8. A fan 9 can be used to keep the pump cool while running. The motor of pump 8 can also include a high temperature shut off to prevent overheating. A pressure switch (not shown) can also be connected to the pump exhaust stream for assuring that the pump is not starved of fluid during operation. Preferably, the pressure switch is set to trip if the exhaust pressure drops below 10 psi. However, other pressure setpoints between 5 and 35 psi are also acceptable. A timer set for 2 minutes allows the machine to generate sufficient pressure to maintain pressure switch activation while operating. This pressure switch uses a pressure activated diaphragm to depress a microswitch when the pressure reaches a fixed pressure limit.

By the action of pump 8, the contaminated fluid next passes through a plugged coupling 10, where spongeballs can be added to the contaminated fluid to assist in mechanically scrubbing the inlet surface of the filtration member housed in the filtration module 11. The plugged coupling is also used to access the system in order to prime pump 8.

The contaminated fluid next passes through filtration module 11, including a filtration member (not shown), to separate the solid particles contained in the contaminated liquid. Although the remaining discussion relates to ultrafiltration modules as an example, any filtration module capable of separating the solid particles from the liquid can be used. For example any type of microfiltration, ultrafiltration, nanofiltration or reverse osmosis filter can be used. One example of an ultrafiltration module includes fifteen ½" outside diameter 0.005 micron tubular membranes arranged in series. The membranes are arranged to create a zig-zag flow pattern where each of the 15 tubes is connected in series to allow liquid to transfer from one tube to another (much like an old carpenter's folded wooden ruler) which provides high filtration efficiency within a small amount of space. Other filter configurations are also acceptable including spiral wound, hollow fiber and layered plate technologies, but these alternatives tend to occupy more space in the machine. The specific example of fifteen 0.005 micron tubular membranes in series is designed to process approximately 2¼ gallons of contaminated liquid per hour.

Any type of filter media can be used in the filtration module. For example, graphite, ceramic and sintered metal members, as well as membrane filters can be used.

The primary high flow exhaust 12 from ultrafiltration module 11 is for the concentrate (i.e., that portion of the contaminated fluid that carries the filtered solid particles). The second low flow exhaust 13 from ultrafiltration module 11 is for the cleansed permeate (i.e., the filtered fluid that passed through the filter membrane of the tubular wall).

The concentrate passes through a second Y-strainer 14, after leaving the ultrafiltration module 11, to remove the spongeballs added to the fluid via plugged coupling 10. A compensating flow control valve 15 is arranged downstream of strainer 14 to throttle the flow rate of pump 8 down to an acceptable level compatible with ultrafiltration module 11. For example, flow control valve 15 can be rated for five gallons per minute. The concentrate is then returned, via conduit 16, to receptacle 2a through nozzle 5.

The permeate passes through a flow gauge 17, which is typically rated from 0 to 25 gallons per hour. The permeate then travels through a charcoal filter 18 to chemically cleanse the fluid of color and restore the solution back to a clear state.

Two inlets of a three-way valve 19 are connected to the outlets of flow gauge 17 and charcoal filter 18, so that the charcoal filter 18 can be by-passed during a cleaning cycle. The outlet of three-way valve 19 feeds the inlet of a second three-way valve 20. The two outlets of three-way valve 20 feed receptacle 2b via conduit 21 and nozzle 5 via conduit 22.

Three-way valve 20 and conduit 22 allow the permeate to be returned and recirculated back to receptacle 2a during multiple-stage filtering operations or for cleaning. In the other position, three-way valve 20 can direct the permeate to the clean receptacle 2b.

Power to the pump 8 is controlled by an electronics box 23 including lighted start 24 and stop 25 switches. Moreover, timers, pressure switches, motor contactors, terminal blocks and auxiliary relays can also be located in electronics box 23.

Triple pipe nozzle 5 will now be explained with reference to FIGS. 2a–b. Nozzle 8 includes a housing 50 with three coaxial tubes 51, 52 and 53 extending from the bottom surface thereof. The upper end of each tube is connected to access ports 51a, 52a and 53a, respectively. Tube 52 is arranged radially outwardly of tube 51, and tube 53 is arranged radially outwardly of tube 52. The axial length of tube 52 is less than that of both inner tube 51 and outer tube 53.

A check-ball valve 54 is positioned at the lower end of inner tube 51. The check ball valve includes a housing 55 in which a check-ball 56 resides. Upward movement of check-ball 56 is limited by a check-ball stop pin 57. Downward movement of check-ball 56 is limited by a check-ball seat 58, which is defined by a bore 59 formed through a concentrate exhaust baffle 60. Concentrate exhaust exit ports 61 are formed through the lower end of outer pipe 53 at a position adjacent concentrate exhaust baffle 60. A permeate redirect baffle 62 is positioned between tubes 52 and 53 at a location above the end of tube 52. Permeate exhaust exit ports 63 are formed through the sidewall of outer pipe 53 at a position adjacent and above permeate redirect baffle 62.

A spring loaded check-ball pull knob 64 is connected to a top end of a stainless steel check-ball release rod 65 having a curved bottom end 65a. Rod 65 is provided to release the check-ball 56 from the check-hall seat 58 to allow the system to drain. System drainage is required, for example, when an empty dirty liquid receptacle 2a is exchanged with a full dirty liquid receptacle 2a of fluid, or when overall system cleaning is necessary. A set screw 66 is also provided in nozzle 50 adjacent the check-ball release rod 65 to maintain the rod 65 in a desired position if so desired, and to plug a drilled access hole for air injection into the sealed system. An O-ring 69 is located between the check-ball release pull knob 64 and nozzle housing 50 to prevent fluid from escaping.

A connection housing 67 is secured to nozzle housing 50, and includes three connector fittings aligned with access ports 51a, 52a and 53a. Specifically, housing 67 includes connectors 68a, 68b, 68c sized to correspond to the sizes of the access ports 51a, 52a and 53a. Each connector 68a–c has an O-ring 69 associated therewith to ensure a water-tight seal between connection housing 67 and housing 50 of nozzle 5. Two stainless steel threaded rods 120 extend from connection housing 67 through nozzle housing 50 and are each provided with a clamping knob 121 having a corresponding threaded brass insert 122 thereby providing, when screwed on to rods 120, the necessary force to maintain the nozzle housing 50 against connection housing 67.

Operating considerations for the recycler of the present invention will next be explained.

PRIMING

In order not to starve the pump of liquid, priming is required before system start-up. Self priming pumps can be used as an alternative for pre-startup liquid priming. Priming entails adding liquid to the inlet line of the pump until it is full of fluid. Priming can be manual or automatic via an auxiliary pump and fluid supply, or a gravity feed line from a clean fluid or permeate tank. The check-ball 56 in the triple pipe assembly in dirty liquid receptacle 2a aids in backflow prevention and reduces the priming refill amount to a minimum. Thus, after the system has been running for a few minutes and then stopped, check-ball 56 and associated housing 55 help prevent drainage of the pump and piping.

Figure 3:
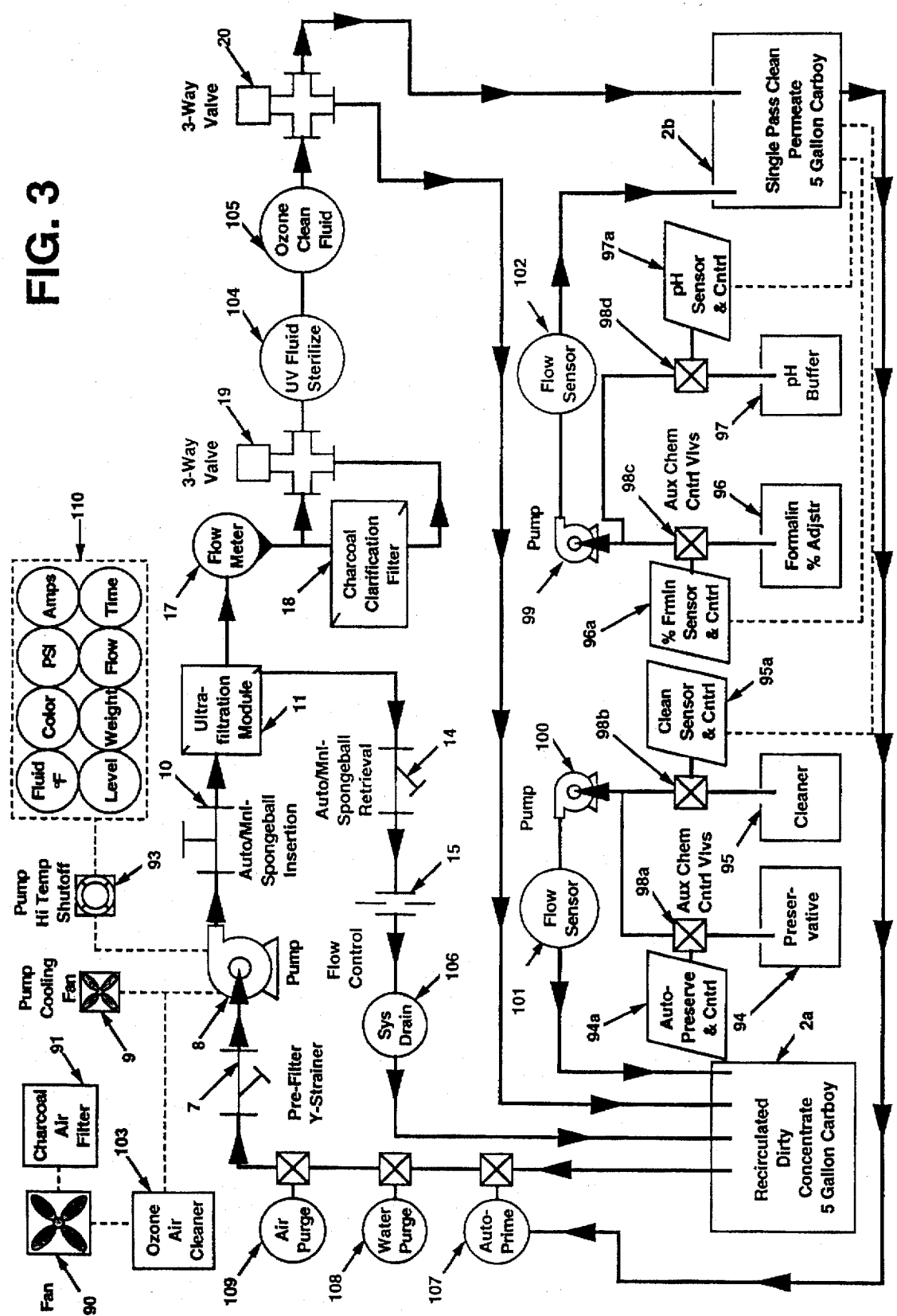
FIG. 3 shows a schematic representation of the present invention.

Automatic priming shown generally by 107 in FIG. 3, can be accomplished by several methods. A first method locates the contaminated liquid tank 2a above the pump suction input port (plugged coupling 10, for example) to allow gravity to prime the pump 8 with liquid, as is explained in the second embodiment of the present invention. A second semi-automatic method can locate a tank of clean or virgin formalin above the priming port (plugged coupling 10, for example) to allow an operator to manually fill the system plumbing. Further, an additional valve and level sensor (not shown) can be used to achieve the same goal automatically.

A third technique uses an auxiliary pump (not shown) to prime the system based on the level of liquid needed. The priming supply fluid should be clean formalin, sourced from a virgin tank or the clean permeate receptacle 2b. Sensors, timers or flow monitors (not shown) can be used with the second or third procedures to fill the system with the proper amount of fluid and to avoid an overfill condition.

LEVEL CONTROL

Receptacle level control can be accomplished in several ways by, for example, monitoring time and flow, gravimetric weight of the receptacles before and after filling, pump supply pressure, ultrasonic sound wave bouncing off the liquid surface, float with mechanical or electrical switch, photoelectric light beam reflecting off of or being broken by the level of fluid, or conductivity or capacitive sensing probes.

FILTER CHANGING

Monitoring of the resultant permeate flow rate after cleaning (explained later herein) can determine when the ultrafiltration module 11 should he changed. If, for example, the flow rate is less than 20% of the flow rate when the ultrafiltration module 11 was new, the module should be exchanged with a new module. Also, monitoring the flow-rate through the pre-filtration Y-strainer 7 indicates at which point the mesh of Y-strainer 7 should be cleaned.

DETERMINING WHEN RECYCLER CLEANING IS NECESSARY

Several methods for determining when system cleaning is required are explained next. Timers based on process run time can shut down the machine and alert an operator as to when and which filter, including ultrafiltration module 11, should be cleaned or exchanged. It is noted that the shape of receptacle 2a influences the ability of the system to self clean. Namely, the suction feed pipe 51 in the dirty liquid receptacle 2a influences system cleanliness by redirecting fluid flow to help sweep sediment and dregs from the tank bottom. In particular, due to the inclined nature of concentrate exhaust baffle 60, shown in FIG. 2a, concentrate flows radially outward from the center of the bottom of receptacle 2a thereby producing eddy currents which disturb any settled particulate.

Another way to detect when cleaning is necessary is to use sensors to detect the permeate flow rate from the main ultrafiltration module 11. Monitoring of differential pressure across any of strainers 7 and 14 and ultrafiltration module 11 can also enhance the accuracy of knowing when to clean. This method gives a more accurate indication as to when system cleaning is required since input fluids can vary in their degree of dirtiness. A color sensor, retroreflective or transmit/receive sensor (not shown) can be placed on the charcoal filter 18 output side to determine when this clarification filter should be replaced. If color is present after the charcoal filter, then an infrared beam can be reflected back to a detector, as in the case of a retroreflective method. The presence of color can block a transmitted infrared beam to its opposing receiving sensor. Lastly, a color sensor can monitor and output a signal based on a lack of clarity or presence of color.

The most effective system for cleaning automatically detects and determines when to put the process through an automatic cleaning cycle. The required cleaning cycle could then be implemented manually from a visual or audible operator alert or could take place fully automatically.

An automatic cleaning indication system utilizes a variety of sensing techniques to ascertain when to cleanse the primary ultrafiltration module 11 with sponge balls, as explained earlier, and cleaning solution. Furthermore, after the system is starved of Formalin (due to the dirty liquid receptacle 2a being empty) and once the cleaning cycle is started, additional sensors (not shown) detect the presence of the appropriate containers and the level of fluid in each container 2a, 2b.

If acceptable conditions exist for the cleaning cycle, electrically or pneumatically controlled three-way valves 19 and 20 are automatically switched to the cleaning position. That is, each valve 19 and 20 is set such that cleaning fluid by-passes charcoal filter 18 and is routed to dirty receptacle 2a. When the cleaning cycle is completed, a water rinse cycle can purge the system of extraneous surfactant and cleaning solvents. An air purge can then help push out remaining water to make way for formalin recycling.

SHUTOFF METHODS

The recycler system can be shutoff by way of numerous methods. Each of the following shutoff methods operates effectively by itself or in combination with others. An optional indicator light (not shown) may be included for indicating the precise reason for machine stoppage. An optional audible alarm or buzzer can also be installed.

Shutoff By Weight: This shutoff method uses the gravimetric weight of the empty or full tank 2a, 2b to shut down the machine and shows when the dirty liquid receptacle tank 2a is empty and/or when the clean permeate tank 2b is full.

Shutoff By Level: This shutoff method uses retroreflective photoelectric, transmit/receive photoelectric, ultrasonic, float level switch, conductivity or capacitance to shut down the machine. The technique can show when the dirty liquid receptacle 2a is empty and/or when the clean permeate tank 2b is full.

Shutoff By Flow: This technique determines shut down time based on a preset flow amount using a flow monitor. Several types of flow monitors or controllers exist. One such device uses a paddle wheel driven by the fluid stream. By counting the revolutions of the wheel, flow rate can be determined.

Shutoff By Time: This method shuts down the machine based on the amount of elapsed process time.

Shutoff By Pressure: This technique uses a pressure switch or transducer (not shown) to monitor the intake or discharge system pressure.

Shutoff By Temperature: This approach uses either electronic or capillary temperature bulbs and controllers (not shown) in the process pump discharge stream to stop the machine when a preset temperature threshold is reached.

Shutoff By Color: In this shut down method the color of the permeate is monitored. If the color is not sufficiently restored an indicator light (not shown) indicates the need to change the charcoal filter and the machine is shut down.

Shutoff By Amperage Draw: According to this technique a sensor (not shown) senses the pump motor amperage load and compares it to an average running current and shuts the system down if the sensed current exceeds a preset threshold.

FIG. 3 is a schematic representation of the recycler system and process as explained with reference to FIGS. 1 and 2a–b, and further includes additional and/or optional features for the recycler of the present invention. The aforementioned additional features may operate automatically or manually.

Fan 90 and charcoal air filter 91 are provided to help purify the air quality around the filtration machine in case of formalin spillage or off-gassing. High temperature shutoff 93 for the pump 8 is shown as well. The other aforementioned shut off methods are also shown collectively as 110.

Auxiliary chemical solutions can be added to the concentrate held in clean receptacle 2b, via metering pump 99 and flow sensor 102, to control the properties of the clean liquid. To control the pH of the solution, for example, an electronic pH sensor and electronic microprocessor 96a control metering pump 99 for adding a pH buffer via control valve 98c, such as sodium acetate held in vessel 96a, for reaching a specific pH goal. Furthermore, the percent formalin can be calculated using electronic sensor 97a and then metering pump 99 can be controlled by sensor 102 to adjust the percentage in clean receptacle 2b using the contents of vessel 97 via control valve 98d.

An automatic cleaning operation referred to earlier herein switches the system from formalin fluid to cleaning solution stored in vessel 95 and circulates the cleaning solution, via valve 98b, pump 100 and sensor 101, for a preset time, temperature or until clean. Sensor 95a may also be used for controlling the cleaning process. The cleaning solution can be sourced from a gravity feed reservoir. Typically, the cleaning solution is concentrated and thus water is added to reach a target dissolution. The recycler system, after the cleaning operation, then purges the cleaning solution to an auxiliary holding tank or flushes it down a drain via system drain 10b. A water hook up and valve 108 can be used to rinse the system of extraneous surfactants, cleaning solvents and residual organic solids. This rinse water can be flushed to an auxiliary holding tank or to an electric evaporator. An optional air purge 109 can also aid in further removal of rinse water.

Also, automatic spongeball insertion and removal can be implemented via coupling 10 and strainer 14 to automatically aid in the cleaning process of the ultrafiltration module 11 by mechanically scrubbing particles trapped on the membrane surface using spongeballs.

If the recycler is not going to be run for a period of time longer than one week, for example, preservative solution is needed to retard bacteria growth and keep the ultrafiltration module 11 moist. Accordingly, after the above-described cleaning operation, a preservative solution held in vessel 94 and piped by pump 100 through control valve 98a and sensor 101, is circulated in the process plumbing and piping for approximately 30 minutes. The preservative will then be in contact with the ultrafiltration module 11.

Figure 4:
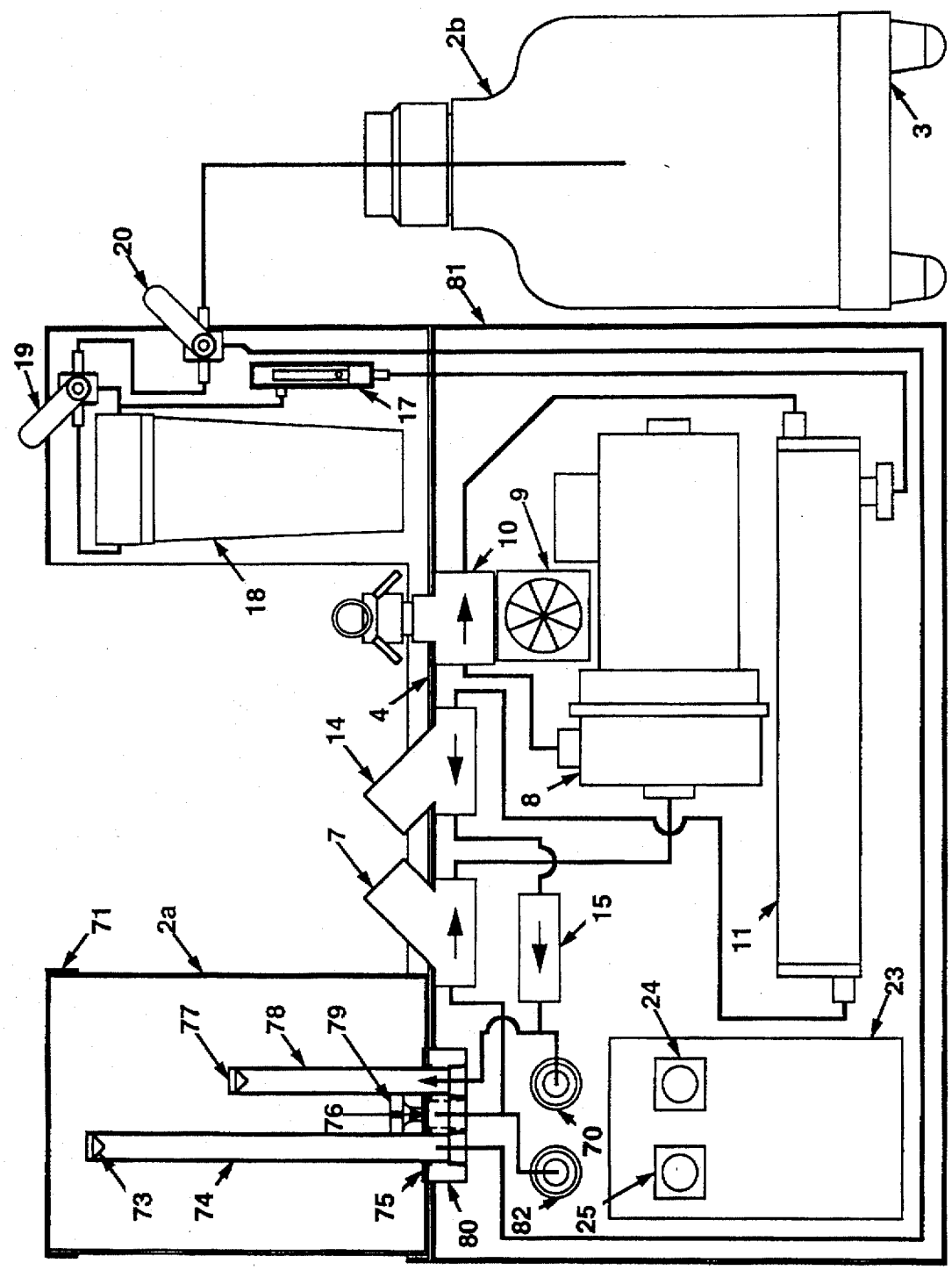
FIG. 4 shows an arrangement of the recycler according to a second embodiment of the invention.

A second embodiment of the invention is shown in FIG. 4 wherein like elements are designated by the same reference numerals. The second embodiment differs from the first embodiment primarily in that the dirty receptacle 2a is located above, and clean receptacle 2b is located adjacent to most of the recycler system components, and in that the triple pipe nozzle 5 is not used. A different pipe arrangement is used instead. All three pipes are now side-by-side and connected to the dirty formalin supply tank 2a versus being separate and telescopic like in the previous embodiment. Only those features which differ from the first embodiment are explained.

As shown in FIG. 4, dirty receptacle 2a, covered by lid 71, is located on Cop of a support base 81 that houses the recycler components. Drip pan 4 is located above housing support base 81. Instead of the coaxial triple pipe nozzle 5 of the first embodiment, dirty tank 2a includes a main system suction inlet 76 connected to a system drain valve 82, normally closed during recycling. The main suction inlet 76 is also connected to Y-strainer 7 as in the first embodiment. A concentrate exhaust pipe 78 with diffuser plug 77, connected to the flow control valve 15, returns concentrate back to the dirty receptacle 2a. This latter pipe is also connected to a fresh water supply valve 70 which is used during recycler system cleaning as explained earlier. Finally, a permeate return pipe 74 with diffuser plug 73 is connected to three-way valve 20 as in the first embodiment such that the formalin being recycled can be processed through the system more than once.

In the second embodiment, flow gauge 17, charcoal filter 18, and the three-way valves associated thereto are, like dirty receptacle 2a, situated above support base 81. Also in this embodiment, clean receptacle 2b is positioned adjacent support base 81 thereby providing easy access thereto.

PURIFICATION OF PERMEATE

In some instances it may be desirable to purify the filtered permeate with additional means shown as elements 104, 105 in FIG. 3. Several methods are available for such a purification step.

One method uses ozone. Ozone is a blue gaseous allotrope of oxygen ($O_3$) formed naturally from diatomic oxygen ($O_2$) by electric discharge or exposure to ultraviolet radiation. It is an unstable, powerfully bleaching, poisonous oxidizing agent with a pungent, irradiating odor, used to deodorize air, purify water, treat industrial wastes and bleach.

The primary application of ozone is to kill harmful bacteria and sterilize products for use. Many different methods exist for producing ozone. The two most common utilize passing air through an ultraviolet light and corona discharge.

Because of its superior cleansing power, ozone can be employed in the recycler of the present invention. An ozone purification process uses a blower or compressed air to pass O2 in front of a special very ultraviolet light for conversion from O2 to O3 (ozone). This ozonated air then flows through a porous media, or diffuser, such as sintered metal or ceramic or a porous membrane, into a formalin bath and percolates to the surface. The porous material helps break up the air flow into tiny bubbles allowing the increased surface area to be more efficient in killing bacteria and purifying the fluid. Another air-to-fluid introduction method is using a forced air venturi and static mixer to uniformly diffuse the ozone throughout the formalin while being pumped through the system piping.

Ozone can also be used to mitigate gaseous fumes. As an alternative or in addition to charcoal air filtration, an ozone air purifier 103 can be used to cleanse the environment of air borne pollutants and odors. Ozone air purification uses similar technology as fluid ozone disinfection, but circulates the air from the fume source, via a blower or fan, through the ozone generator and then back to the surrounding environment or to an exhaust vent.

Yet another purification technique utilizes ultraviolet light as indicated by element 104 in FIG. 3. The use of ultraviolet light can help sterilize the fluid during processing. Possible configurations can include passing a thin sheet of fluid in front of an ultraviolet light or running fluid around a waterproof ultraviolet light to allow as much surface area of the liquid to be exposed as possible.

OTHER FEATURES

Recycler configurations can include vertical free-standing, horizontal free-standing, mobile cart, wall mount, and counter top. As previously explained, feeding options allow for top gravity feed (via inverted jug or drain spigot on carboy bottom), bottom feed, manual fill and auto fill (from remote tank). Front or back interior access to the housing 1a, 1b can be with or without a panel or door. A back panel can be with or without louvers, holes or slits to allow hot air from the pump 8 to escape. Of course, the recycler can have different cosmetics and esthetics by utilizing different unpainted, painted or anodized colors on steel, aluminum or stainless steel. The machine shape can he round, square, rectangular or contemporary. Finally, the top can be flat, beveled or with a console, like on a dishwasher.

The invention has been described with reference to certain preferred embodiments thereof. It will be understood, however, that variations and modifications are possible within the scope of the appended claims. For example, many of the sensors mentioned above are not explained in detail since one skilled in the art would readily know how to implement appropriate sensors throughout all phases of the recycler of the present invention.

Moreover, while the present invention has been explained with reference to a specific application, Formalin recycling, it can be implemented with various types of other hazardous fluids that contain particles to be removed.

What is claimed is:

1. A method of recycling a fluid consisting essentially of formalin, comprising the steps of:

pumping a particle-containing formalin fluid from a dirty tank through a first strainer or pre-filter thereby removing large particles;

filtering the fluid through a filtration module to remove finer particles not strained by said strainer or pre-filter;

and routing permeate resulting from said filtering step to one of the dirty tank, a clean tank and a charcoal filter.

2. The method of claim 1, further comprising charcoal-filtering the permeate resulting from said filtering step.

3. The method of claim 1, further comprising inserting spongeballs prior to said filtering step and retrieving said spongeballs after said filtering step.

4. The method of claim 1, further comprising controlling a flow of concentrate flowing out of the filtration module.

5. The method of claim 1, further comprising gauging the flow of permeate resulting from said filtering step.

6. The method of claim 1, further comprising controlling at least one of the pH and percent formalin of said permeate.

7. The method of claim 1, further comprising purifying the formalin with ozone.

8. The method of claim 1, further comprising purifying the formalin with ultraviolet light.

9. The method of claim 1, further comprising purifying fumes with one of ozone and charcoal.

10. The method of claim 1, wherein the filtering step is performed at room temperature.

11. The method of claim 1, wherein the fluid is maintained at a temperature below its vapor or distillation temperature.

\* \* \* \* \*